United States Patent [19]

Takahashi et al.

[11] Patent Number: 5,007,995
[45] Date of Patent: Apr. 16, 1991

[54] DEVICE FOR ELECTROFUSION OF CELLS

[75] Inventors: Yasuo Takahashi, Drexelhill, Pa.;
Kazuo Suzuki, Stony Brook, N.Y.;
Toshinobu Niimura, Port Jefferson, N.Y.; Tokio Kano, Nesconset, N.Y.

[73] Assignee: Olympus Optical Co., Ltd., Tokyo, Japan

[21] Appl. No.: 350,715

[22] Filed: May 11, 1989

[51] Int. Cl.$^5$ .............................................. C12N 13/00
[52] U.S. Cl. .............................. 204/299 R; 204/183.1;
435/173; 435/273; 935/85; 935/89; 935/93
[58] Field of Search ......................... 204/183.1, 299 R;
435/172.1, 172.2, 172.3, 173, 287; 935/52, 85, 89, 93

[56] References Cited

U.S. PATENT DOCUMENTS

| | | | |
|---|---|---|---|
| 4,081,340 | 3/1978 | Zimmermann et al. | 204/299 R |
| 4,154,668 | 5/1979 | Zimmermann et al. | 204/299 R |
| 4,441,972 | 4/1984 | Pohl | 204/299 R |
| 4,476,004 | 10/1984 | Pohl | 204/299 R |
| 4,578,168 | 3/1986 | Hofmann | 204/183.1 |
| 4,663,292 | 5/1987 | Wong et al. | 435/287 |
| 4,822,470 | 4/1989 | Chang | 204/299 R |

FOREIGN PATENT DOCUMENTS

| | | |
|---|---|---|
| 3507398 | 9/1986 | Fed. Rep. of Germany . |
| 62-151174 | 7/1987 | Japan . |
| 64-2566 | 1/1989 | Japan . |

*Primary Examiner*—John F. Niebling
*Assistant Examiner*—David G. Ryser
*Attorney, Agent, or Firm*—Kenyon & Kenyon

[57] ABSTRACT

A device and a method for fusing biological cells. The device is formed by a chamber having a tube for containing a cell suspension and a cover for sealing the tube. The chamber is provided with a lower electrode having a smooth and flat surface for contacting the cells precipitating in the cell suspension, and an upper electrode opposite to the lower electrode. The lower electrode forms the inner bottom surface of the tube. The upper electrode is inserted in the cover to enter the tube. The chamber is centrifuged to form the layers of cells on the lower electrode at the bottom of the tube. Then, a predetermined ac voltage is applied across the upper and lower electrodes to fuse the cells efficiently. Such a device and method are useful for the production of monoclonal antibodies or giant cells.

6 Claims, 5 Drawing Sheets

1

DEVICE FOR ELECTROFUSION OF CELLS

BACKGROUND OF THE INVENTION

1. Field of the Invention

The present invention relates to a device and a method for fusing biological cells in a cell suspension, more particularly to a chamber for fusing cells without using dielectrophoresis and to a method of fusing cells by electroporation without using a dc pulse.

2. Description of the Related Art

Cell fusion is useful for the production of monoclonal antibodies or giant cells, or the introduction of a high molecular weight substance into a cell.

Conventionally, a method of cell fusion by chemical adhesion using polyethylene glycol (PEG) has been frequently used. However, since PEG is toxic to cells, fusion yields will be dependent on the quality of PEG. With most PEG, the ratio of formed hybridoma to lymphocytes is $1:2 \times 10^5$, and with the most effective PEG, the ratio is $1:5 \times 10^4$ (S. Fazekas de St. Grouth and D. Scheidegger, J. Immunol, Method, 35, 1, 1980).

In recent years, electroporation, a method of applying a high voltage pulse to make pores in cell membranes, has been used for cell fusion or the introduction of a gene. The cell fusion method using electroporation is called electrofusion, electro-cell-fusion, etc. This method includes a first step of contiguously aligning cells in a cell solution between a pair of electrodes, and a second step of applying a high voltage pulse to the contiguously aligned cells.

U.S. Pat. No. 4,441,972 discloses a cell fusion method using a chamber defined by two parallel upper and lower electrode plates. In the first step, dielectrophoresis is performed with a weak ac voltage (1 to 20 volts, 200 to 600 kHz) to form pearl chains of cells between the parallel electrode plates. Then, in the second step, electroporation is carried out with a brief dc pulse (10 to 250 volts, 1 to 200 microsec).

European Patent Application, Publication No. 193769 discloses a method using a reaction tube applied to a centrifuge. In the first step, precipitated cell layers are formed at the bottom of the reaction tube by centrifugation. In the second step, a pair of electrode are inserted in the reaction tube, and electroporation is effectuated with a short dc pulse (2.5 to 5.0 kV/cm, 30 microsec).

In commonly used cell fusion apparatus, the ac voltage used for dielectrophoresis is in the range of 40 to 200 $V_{p-p}$ and 0.25 to 20 MHz, and the dc voltage used for electroporation is in the range of 200 to 3,000 V and 0.1 microsec to 100 ms. However, the method using dielectrophoresis requires a two-step treatment with ac and dc power so that its construction is complicated. On the other hand, in the method using centrifugation, it is difficult to reproduce the optimum arrangement between the cells and the electrodes because the electrodes are inserted after centrifugation. Further, in the electroporation using a dc pulse, the reproducibility of the voltage condition is low because of an unstable pulse wave having overshoot or ringing, so that a high-level control means is necessary.

SUMMARY OF THE INVENTION

An object of the present invention is to provide an apparatus for fusing biological cells without using dielectrophoresis, the apparatus being very efficient and simply constructed.

Another object of the invention is to provide a method of fusing biological cells by electroporation with stable stimulation, the method being suitable for using the above apparatus and easy to control.

In order to attain these objects, the present invention provides a device for fusing biological cells comprising a tube having an upper open end, a lower open end, and a side wall between the upper and lower open ends; a lower electrode having a flat surface attached tightly to the lower open end of the tube; a cover mounted tightly and detachably on the upper open end of the tube; and an upper electrode penetrating through the cover and extending to the vicinity of the flat surface of the lower electrode with a space remaining between the upper electrode and the side wall of the tube. In a preferred embodiment, the central axis of the tube is straight, and the upper electrode is rod-shaped. The word "vicinity" means a distance of about 0.1 to 2.0 mm.

Further, the present invention provides a method of fusing biological cells comprising the steps of supplying a solution containing cells to be fused to a pair of electrodes; aligning at least two of the cells with one of the pair of electrodes; applying one or more alternating current signals of at least 5 kV/cm and an application time of 100 to 2000 microsec across the pair of electrodes; and cultivating in a medium the cells to which the signals were applied. In a preferred embodiment, the ac signals have a frequency of 5 to 100 kHz.

With the apparatus and method of the present invention, it is possible to supply a sufficient quantity of suspension in the space between the tube and the upper electrode and to move the cells in the suspension toward the lower electrode for contiguous alignment, without being obstructed by the upper electrode, since in the tube the lower electrode closes up in the vertical direction the lower opening of the tube with the flat surface and the upper electrode extends from the upper opening to the vicinity of the lower electrode with the space remaining between the upper electrode and the inside wall of the tube. Further, it is possible to perform the cell fusion by electroporation which is stable and easy to control, since an ac signal is used instead of a dc pulse.

DESCRIPTION OF THE PREFERRED EMBODIMENTS

Figure 1:
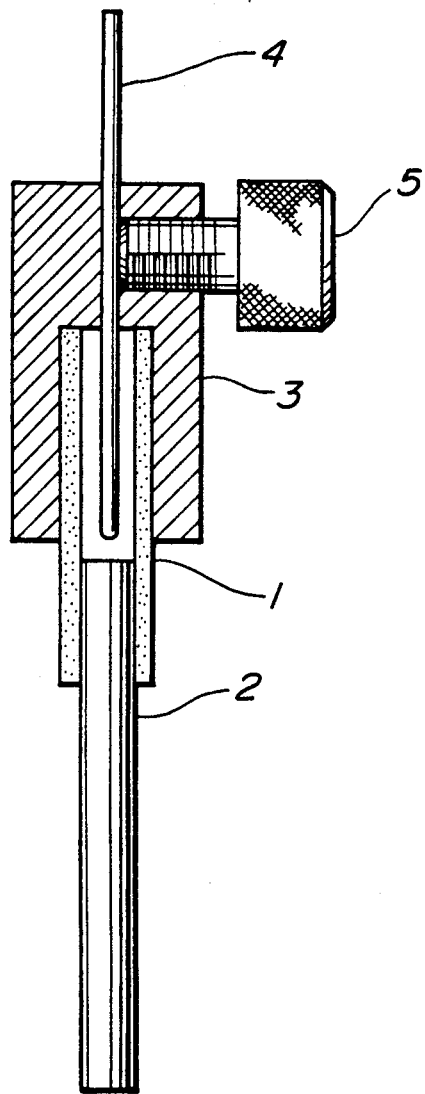
FIG. 1 is a sectional view of a chamber for cell fusion according to the present invention.

FIG. 1 shows a chamber used in the present invention. A tube 1 has an upper open end and a lower open end aligned with the straight central axis and is made of a heatproof and chemical-resisting material, such as glass, Teflon, polyester, polypropylene, polycarbonate, etc. The size of the lower open end of the tube 1 is preferably 2.0 to 4.0 mm in diameter and 10.0 to 20.0 mm long.

A lower electrode 2 is made of an electrochemically stable material, such as platinum, gold, stainless steel, tin oxide, silver, carbon, etc. The lower electrode 2 has almost the same diameter as that of the lower open end and is long enough, preferably 20.0 to 50.0 mm. The upper end surface of the lower electrode 2 is flat and smooth and perpendicular to the central axis of the tube 1. The lower end of the lower electrode 2 is secured to the lower open end of the tube 1 tightly by sealing, fusing or melting so as to form the bottom of a space in the tube 1 to contain at least 20 µl of a suspension. The lower electrode 2 protrudes from the lower end of the tube 1 substantially.

A cover 3 made of a material similar to that of the tube 1 has a diameter larger than that of the upper open end of the tube 1. The cover 3 is mounted with its concave part tightly and detachably on the upper end of the tube 1.

An upper electrode 4 made of material similar to that of the lower electrode 2 is inserted in the cover 3 so that it may slide along the central axis of the tube 1. The upper electrode 4 has a cross section smaller than that of the lower open end of the tube 1. The lower end of the upper electrode 4 extends to the vicinity of the lower electrode 2. Preferably, the lower end of the upper electrode 4 has a spherical or semispherical end surface. Further, it is preferable that the side wall of the cover 3 is provided with a hole in which an adjustable screw 5 is screwed to secure the upper electrode 4 inserted in the cover 3.

Figure 2A:
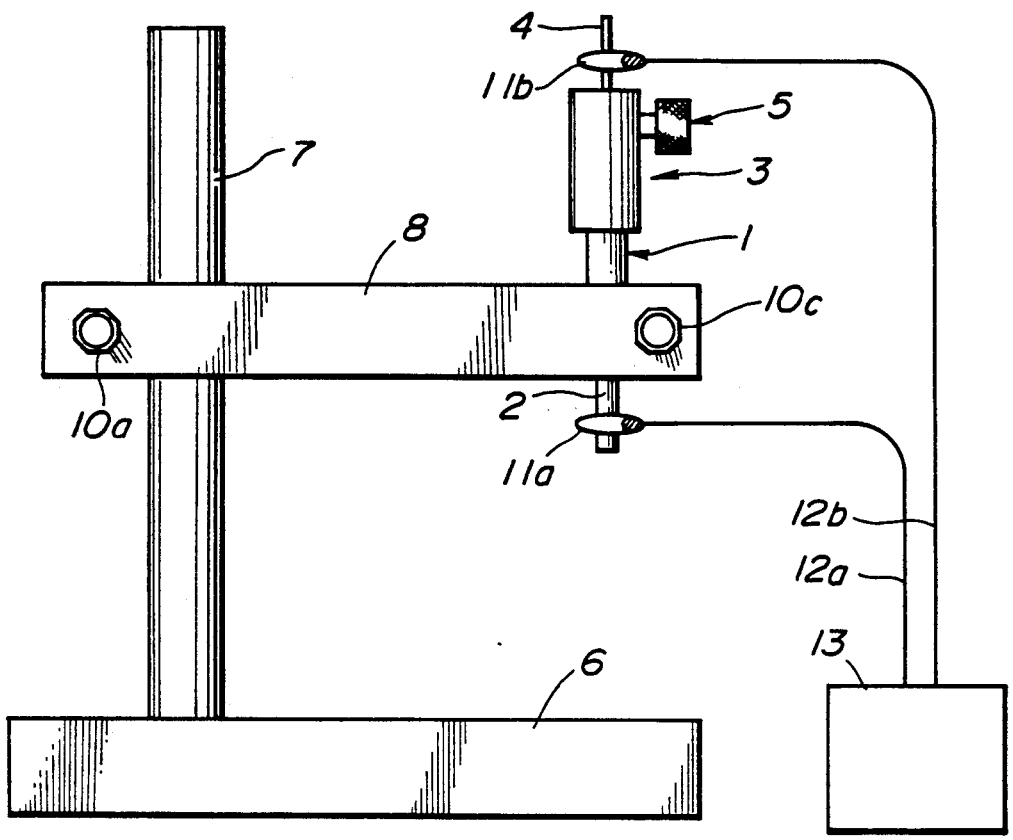
FIGS. 2a and 2b are elevation and plan views of a stand supporting the chamber of FIG. 1 to apply an ac signal.
Figure 2B:
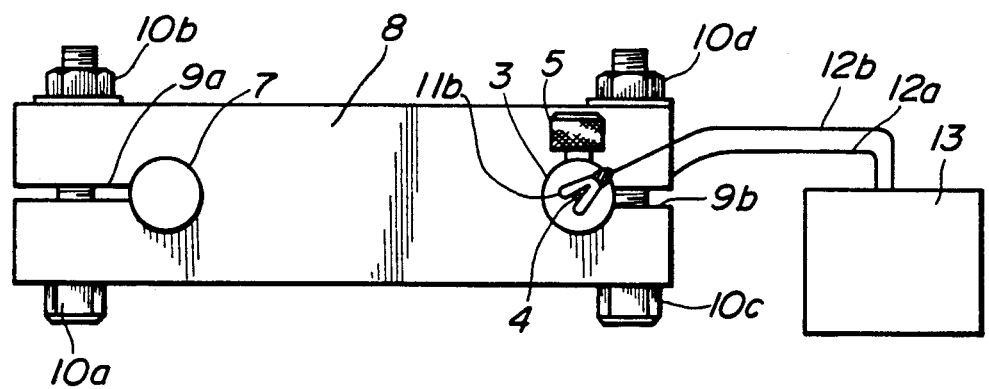

FIG. 2 shows a stand for supporting vertically the chamber shown in FIG. 1. A supporting pole 7 is vertically fixed to a base 6. A holding rod 8 made of a flexible insulating material is provided at its ends with vertical splits 9a and 9b including holes through which the supporting pole 7 and the lower electrode 2 of the chamber can be inserted, respectively. Bolts and nuts 10a to 10d are used to tighten the splits 9a and 9b. The holding rod 8 is fixed to the upper portion of the supporting pole 7 via the split 9a. The lower electrode 2 of the chamber is fixed to the holding rod 8 via the split 9b. The lower electrode 2 protruding downward from the holding rod 8 and the upper electrode 4 protruding upward from the cover 3 are clamped with adapters 11a and 11b, such as zigzag clips, which are connected to an ac signal supplier 13 via lead wires 12a and 12b, respectively. The ac signal supplier 13 is a combination of known devices such as an ac power source, a power amplifier, a function generator, a trigger circuit, etc.

Now, the operation of the above apparatus will be described. A predetermined quantity of a suspension containing cells to be fused is fed into the inner space of the chamber by a pipette, etc, and the upper open end of the tube 1 is tightly capped with the cover 3. Then, the adjustable screw 5 in the cover 3 is loosened, the upper electrode 4 is moved axially so that its lower end is at such a distance from the lower electrode 2 as is necessary to obtain an enough voltage between the upper and lower electrodes 4 and 2, and the upper electrode 4 is secured again by the adjustable screw 5. Subsequently, the chamber is set in a centrifuge with the longitudinal direction of the tube 1 being in the direction of centrifugation. The camber can be easily set in the centrifuge by means of a centrifuge tube having a diameter larger that those of the tube 1 and the cover 3, or a microtitreplate having a vertical hole for holding the tube 1 or the lower electrode 2. After the centrifuge is operated for a predetermined time, the chamber is removed from the centrifuge. The lower electrode 2 is inserted in the hole of the split 9b and secured to the holding rod 8 by screwing the bolts and nuts 10c and 10d. The adapters 11a and 11b are applied to the lower end of the lower electrode 2 and to the upper electrode 4, respectively, and the ac signal supplier 13 is activated. The voltage generated by the ac signal supplier 13 is applied to the lower and upper electrodes 2 and 4 through the lead wires 12a and 12b, respectively, to fuse the cells in the chamber.

Figure 3:
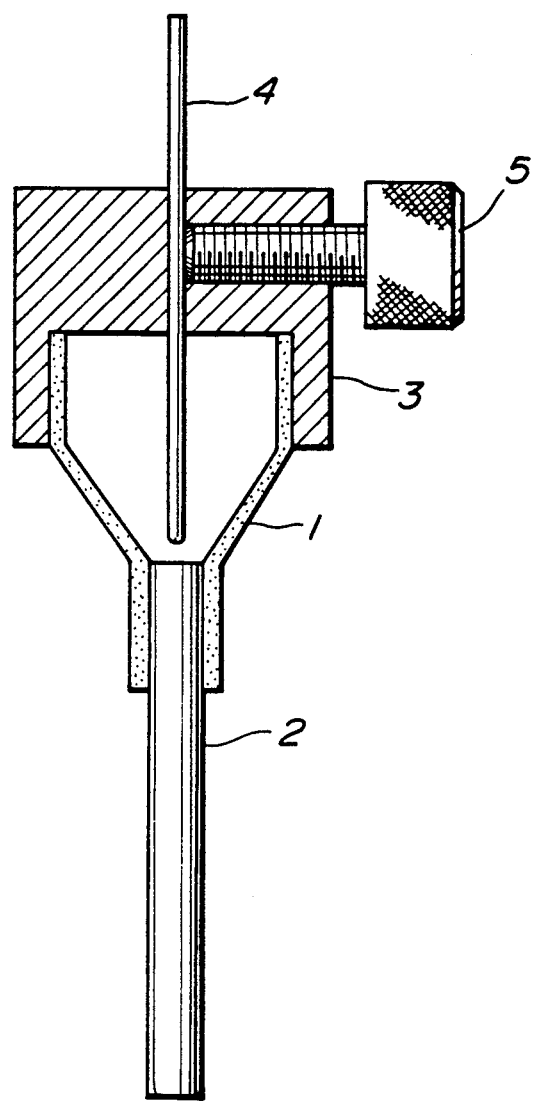
FIG. 3 is a sectional view of another chamber for cell fusion according to the present invention.

FIG. 3 shows a chamber formed by the same members as those of the chamber of FIG. 1, except that the side wall of the tube 1 is gradually expanded from the upper end of the lower electrode 2. When the same quantities of cell suspension are dispensed to the chambers of FIGS. 1 and 3, the level of the suspension in the chamber of FIG. 3 is lower than that in the chamber of FIG. 1. Therefore, with this chamber, it is possible to shorten the time for centrifugation.

Figure 4:
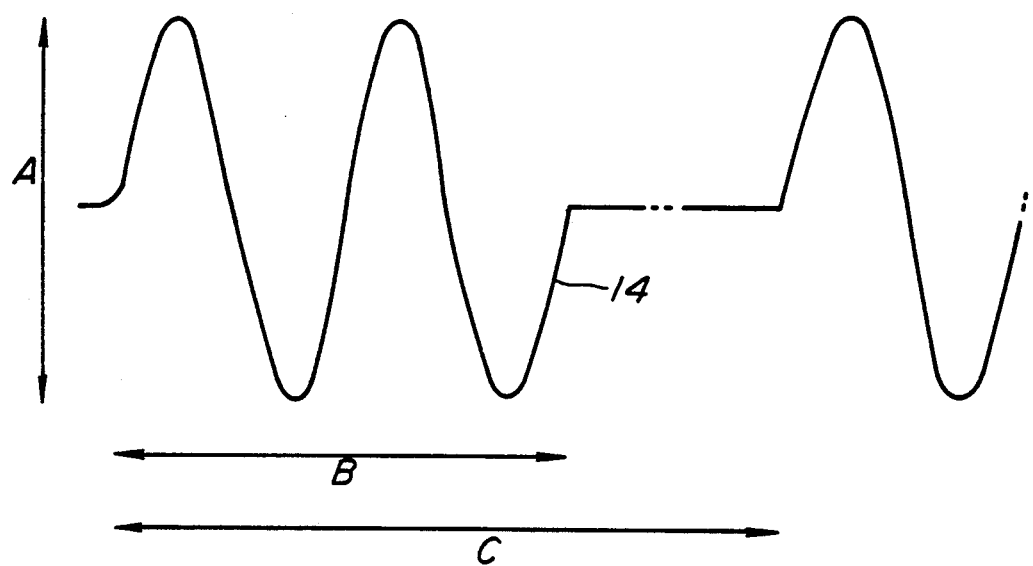
FIG. 4 is a graph showing a wave form of an ac signal used for the cell fusion method of the present invention.

FIG. 4 shows an ac signal 14 used for the cell fusion method of the present invention. The ac signal 14 having a predetermined frequency and voltage A forms at least one cycle of a sine wave within the application time B and is repeatedly generated at stimulation intervals C as many times as necessary. The frequency, voltage A and application time B of the ac signal 14 are predetermined to carry out a proper electroporation for the particular cells to be fused. The ac signal 14 has a continuous wave form and thus is easy to control so that it is possible to perform electroporation of cells by stable stimulation.

The chamber shown in FIG. 1 was made in the following manner:

EXAMPLE 1

The lower electrode 2 was made of stainless steel of a cylindrical form having a diameter of 3.8 mm and a length of 23.0 mm, and one end surface of the lower electrode 2 is finished to be a smooth plane perpendicular to its axis. The lower electrode 2 with its finished end surface upward was inserted with the adhesive Alontight into the lower open end of the tube 1 by 5.0 mm and bonded to the lower open end, the tube 1 being made of glass of a cylindrical form having an inner diameter of 4.0 mm, an outer diameter of 6.0 mm and a length of 15.0 mm. The gap between the upper end edge of the lower electrode 2 and the tube 1 was filled with the adhesive Alonalpha (Toagosei Chem. Ind. Co., Ltd.). A cylindrical space of a diameter of 6.6 mm and a depth of 9.0 mm was cut out in the center of one end surface of the cover 3 made of Teflon of a cylindrical form having a diameter of 11.0 mm and a length of 17.0 mm, and an axial hole of a diameter of 1.4 mm was provided from the center of the cylindrical space to the center of the other end surface of the cover 3. Further, a hole for the adjustable screw 5 was made in the side wall of the cover 3 in such a manner that the hole is perpendicular to the axial hole. Then, the upper electrode 4 was made of stainless steel of a rod form having a diameter of 1.0 mm and a length of 26.0 mm, and its one end was polished to have a semispherical surface. The upper electrode 4 was inserted in the axial hole of the cover 3 with the one end extending into the cylindrical space. The small screw 5 was driven in the hole of the cover 3 by a screwdriver to secure the upper electrode 4. The cover 3 with its cylindrical space downward was mounted on the upper open end of the tube 1. The adjustable screw 5 was loosened, and the upper electrode 4 was moved up and down so that its lower end was positioned at a predetermined distance from the lower electrode 2 while measuring the distance with a pair of slide calipers. Then, the adjustable screw 5 was secured again.

Next, the method of the present invention will be described on the basis of the following examples.

EXAMPLE 2

Production of anti-HSA monoclonal antibody (1) Preparation of a cell suspension

Female BALB/C mice, 6 weeks of age, were injected with 10 μg HSA (human serum albumin) in Freund's adjuvant, and this was repeated 5 times at 3-week intervals. Three days after the last injection with 5 μg HSA in phosphate buffer solution (PBS), the spleen was removed, and lymphocytes were obtained by separating red blood cells with the method of density gradation centrifugation. A cell suspension was prepared in such a manner that $9 \times 10^6$ lymphocyte cells were mixed with $9 \times 10^5$ myeloma cells (P3-X63-Ag8.653) in 75 μl of glucose-phosphate buffer solution.

(2) Electrofusion of cells

75 μl of the prepared cell suspension was supplied into the tube 1 of the chamber. After capping the tube 1 with the cover 3, the distance between the lower electrode 2 and the upper electrode 4 was adjusted to 0.5 mm. The chamber was then set in a centrifugation device (Beckman GRP) with the protruding part of the lower electrode 2, and the cell suspension was subjected to centrifugal separation at 120 g. Immediately thereafter, the chamber was transferred to the holding rod 8 of the stand as shown in FIG. 2, and an ac signal (12 kV/cm, 10 kHz, 200 microsec, room temp.), the wave form of which is shown in FIG. 4, was applied 10 times at regular intervals of 1 second with the ac signal supplier 13 comprising a power amplifier (ENI 1140 LA) and a function generator (TEK FG501A). 5 minutes later, the cells in the chamber were dispensed evenly into 12 or 18 wells of a 96-well microtitreplate with each 100 μl of HAT medium for selecting hybridoma cells. After 1 week incubation at 37° C., the number of hybridoma colonies formed in the wells was counted. At that time, the number of colonies which formed an overlapped linkage consisting of at least 10 individuals in a well was considered as 10. The supernatant was supplied into wells coated with HSA, and absorbance was measured at 490 nm using EL 311 (BIO-TEK Instr., Inc.) after the reactions with peroxidase-labelled goat antimouse (IgG+IgM) and subsequently with o-phenylene diamine according to the method of EIA (enzyme immunoassey). The results are shown in Table 1.

TABLE 1

| Exp. No. | Well No. | No. of Colonies | Absorbance OD 490 |
| --- | --- | --- | --- |
| 1 | 1 | 10 | ***** |
|  | 2 | 6 | 2.436 |
|  | 3 | 8 | ***** |
|  | 4 | 10 | ***** |
|  | 5 | 10 | ***** |
|  | 6 | 10 | 1.392 |
|  | 7 | 5 | ***** |
|  | 8 | 3 | 2.970 |
|  | 9 | 4 | 1.164 |
|  | 10 | 5 | ***** |
|  | 11 | 6 | ***** |
|  | 12 | 2 | 0.909 |
| 2 | 1 | 3 | 0.846 |
|  | 2 | 2 | 1.575 |
|  | 3 | 4 | 1.610 |
|  | 4 | 6 | 1.678 |
|  | 5 | 5 | 2.724 |
|  | 6 | 3 | 2.244 |
|  | 7 | 3 | 2.047 |
|  | 8 | 4 | 2.651 |
|  | 9 | 5 | 0.868 |
|  | 10 | 10 | 0.741 |
|  | 11 | 6 | 1.011 |
|  | 12 | 5 | 0.648 |
| 3 | 1 | 10 | 0.652 |
|  | 2 | 10 | 0.502 |
|  | 3 | 10 | 0.465 |
|  | 4 | 10 | 0.449 |
|  | 5 | 10 | 0.769 |
|  | 6 | 10 | 2.433 |
|  | 7 | 10 | 1.240 |
|  | 8 | 10 | 0.977 |
|  | 9 | 10 | 0.674 |
|  | 10 | 10 | 0.460 |
|  | 11 | 10 | 0.325 |
|  | 12 | 10 | 0.972 |
|  | 13 | 10 | 0.362 |
|  | 14 | 10 | 1.984 |
|  | 15 | 10 | 2.042 |
|  | 16 | 10 | 0.506 |
|  | 17 | 10 | 1.071 |
|  | 18 | 10 | 0.496 |
| 4 | 1 | 10 | 0.508 |
|  | 2 | 10 | 2.755 |
|  | 3 | 10 | 0.745 |
|  | 4 | 10 | 2.152 |
|  | 5 | 10 | 2.702 |
|  | 6 | 10 | 0.736 |
|  | 7 | 10 | 0.557 |
|  | 8 | 10 | 0.841 |
|  | 9 | 10 | 0.621 |
|  | 10 | 10 | 0.817 |
|  | 11 | 10 | 0.792 |
|  | 12 | 0 | — |
| 5 | 1 | 10 | 0.876 |
|  | 2 | 10 | 0.607 |
|  | 3 | 10 | 0.926 |
|  | 4 | 10 | 0.535 |
|  | 5 | 10 | 2.295 |
|  | 6 | 10 | 0.577 |
|  | 7 | 10 | 0.722 |
|  | 8 | 10 | 1.755 |
|  | 9 | 10 | 1.082 |
|  | 10 | 10 | 0.793 |
|  | 11 | 10 | 0.488 |
|  | 12 | 10 | 0.564 |

The mark ***** represents that the value is over the measuring range.

According to the results of Exps. 3 to 5, the ratio of formed hybridoma cells to lymphocytes is $1:7.4 \times 10^4$.

(3) Specificity

The colonies in the wells of the above Exps. 1 and 2 were cloned three times by the limiting dilution method, and then it was examined whether they were reactive to different kinds of substances. The isotype of the antibody produced by the hydridoma cells was also examined by Ouchterlony's method. The results are shown in Table 2.

TABLE 2

| Exp. No. | Well No. | Isotype | HSA | Gelatin | BSA | Human IgG |
|---|---|---|---|---|---|---|
| 1 | 1 | IgG 1 | + | — | — | — |
| 1 | 4 | IgG 1 | + | — | — | — |
| 1 | 5 | IgG 1 | + | — | — | — |
| 1 | 7 | IgG 1 | + | — | — | — |
| 1 | 10 | IgG 1 | + | — | — | — |
| 2 | 5 | IgG 1 | + | — | — | — |
| 2 | 6 | IgG 1 | + | — | — | — |
| 2 | 7 | IgG 1 | + | — | — | — |
| 2 | 8 | IgG 1 | + | — | — | — |

All of 9 colonies used were reactive to HSA specifically, but there was no cross-reaction with bovine serum albumin (BSA), gelatin and human IgG. All of the isotypes of the obtained hybridoma cells were IgG 1.

EXAMPLE 3

In this example, a cell suspension was prepared and an ac signal was applied in the same manner as in Example 2. This example differs from Example 2 only in that myeloma cells were used as feeder cells in cultivation. The cells to which the ac signal had been applied as in Example 2 were kept still in the chamber for 5 minutes. Then, all of the cells were taken out by a pipette, mixed with 2 ml of an HT medium (hypoxanthine, thymidine, 20% FBS-D-MEM) including $1 \times 10^6$ myeloma cells (P3-X63-Ag8.653), and stirred slowly. 100 $\mu$l of the mixture was dispensed to each of 20 wells of a 96-well microtitreplate. One day later, 100 $\mu$l of an HAT medium was dispensed to each well. The hybridoma colonies formed in each well after one week's incubation at 37° C. were counted. 20 hybridoma colonies per well of the microtitreplate were found. Therefore, the ratio of formed hybridoma colonies to lymphocytes was $1:2.3 \times 10^5$.

EXAMPLE 4

This example differs from Example 2 only in that lymphocytes and myeloma cells were mixed in the ratio of 1 to 1 when cells were prepared. Immunization was carried out and lymphocytes were obtained in the same way as in Example 2. A cell suspension was prepared by mixing $9 \times 10^5$ lymphocytes and $9 \times 10^5$ myeloma cells (P3-X63-Ag8.653) with 75 $\mu$l of glucose-phosphate buffer solution. The cell suspension was centrifuged in the same manner as in Example 2, and an ac signal was applied. After the suspension was kept still for 5 minutes, the cells in the chamber and each 100 $\mu$l of an HAT medium were equally dispensed to each of 10 wells of a 96-well microtitreplate. The hybridoma colonies formed in each well after one week's incubation at 37° C. were counted. 9 hybridoma colonies per well of the microtitreplate were found. Therefore, the ratio of formed hybridoma colonies to lymphocytes was $1:1 \times 10^4$.

EXAMPLE 5

Cell fusion test under various conditions of electric field (1) Preparation of a cell suspension Lymphocytes were obtained from the spleen of a six-week-old male BALB/C mouse which had not been immunized. Red blood cells obtained together with the lymphocytes were eliminated by incubation in 0.17 M NH4Cl at 4° C. for 10 minutes. Mouse myeloma cells (P3-X63-Ag8) cultivated in D-MEM solution containing 10% fetal bovine serum (FBS) were used. These lymphocytes and myeloma cells were resuspended in D-MEM solution without FBS, and the suspension containing $5 \times 10^6$ lymphocytes and $5 \times 10^7$ myeloma cells was centrifuged and mixed. After removing the supernatant, 500 $\mu$l of cell suspension containing 1 mM PBS, 0.5 mM manganese acetate and 280 mM inositol was prepared.

(2) Cell fusion

25 $\mu$l of the prepared cell suspension was dispensed into the tube 1 of the chamber in FIG. 1. The tube 1 was capped with the cover 3, and the distance between the lower and upper electrodes 2 and 4 was adjusted to 0.5 mm by the adjustable screw 5. In the same manner as in Example 2, the chamber was subjected to centrifugation at 100 g for 5 seconds and immediately fixed to the holding rod 8 in FIG. 2. Under various conditions, an ac signal was applied across the lower and upper electrodes 2 and 4 at room temperature. After applying the electric field, the chamber was kept still for 5 minutes. The cells in the chamber were then added to 2 ml HT solution (hypoxanthine, thymidine, 20% FBS-D-MEM) including $5 \times 10^5$ suspended myeloma cells/ml as feeder cells and mixed slowly. Each of 20 wells of a 96-well plate were filled with 100 $\mu$ml of the mixture. After incubation at 37° C. for 24 hours, 100 $\mu$l HAT solution was added to each well, and the incubation was continued. One week later, the number of hybridoma colonies formed in each well was counted. The results are shown in FIGS. 5 to 8. The vertical axis of each figure represents the number of hybridoma colonies per $2.5 \times 10^5$ myeloma cells when the electric field was applied. The horizontal axis represents a parameter of electric field conditions, and the parenthesized numbers denote the times of test carried out at the value. The curve in each graph was drawn statistically on the basis of the value of mean $\pm$ME.

A. Voltage condition

Figure 5:
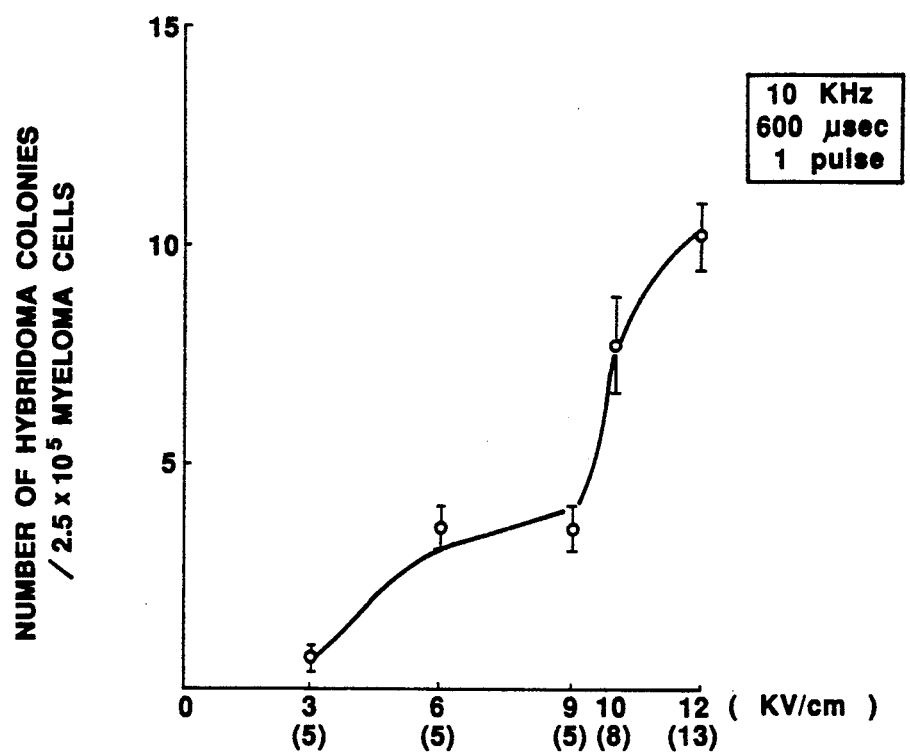
FIG. 5 is a graph showing a relationship between the voltage and hybridoma forming rate when an ac signal is applied to the chamber as shown in FIGS. 2a and 2b.

FIG. 5 shows the forming rate of hybridoma colonies obtained by applying to the chamber of FIG. 1 after centrifugation an ac signal having a frequency of 10 kHz, the application time being 600 microsec, the number of applied stimulation being 1, the voltage of the ac signal being a variable. At 3 kV/cm, few hybridoma colonies were formed. From 6 to 9 kV/cm, 3 to 4 colonies per $2.5 \times 10^5$ myeloma cells were obtained. Near 9 to 10 kV/cm, the number of hybridoma colonies increased sharply (7 to 9 hybridoma colonies/$2.5 \times 10^5$ myeloma cells), and at 12 kV/cm, the forming rate increased more. It is assumed that the application of an ac voltage of 10 kV/cm or more caused the layers of cells on the lower electrode 2 to be pressed vertically to promote the cell fusion. The largest strength of electric field producible in the chamber of FIG. 1 was 12 kV/cm. When the distance between the pair of electrodes was smaller than 0.5 mm, only the center of the surface of the lower electrode 2 received the effect of the electric field so that it became difficult to fuse the cells in the peripheral area.

B. Frequency condition

Figure 6:
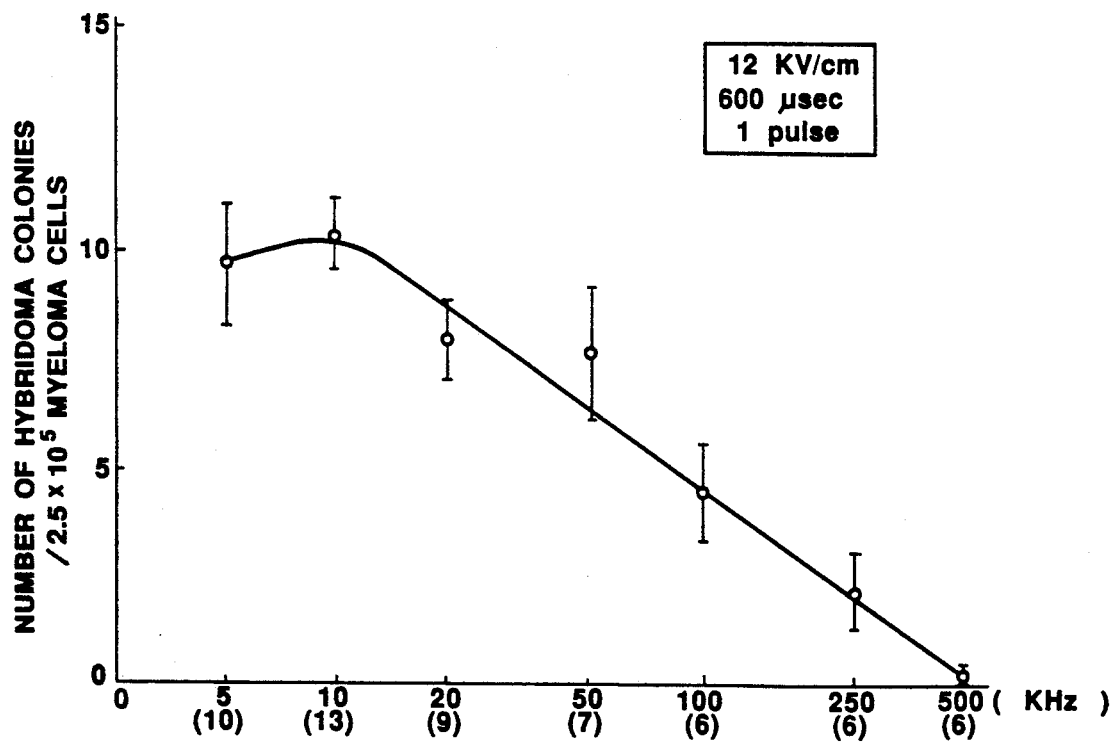
FIG. 6 is a graph showing a relationship between the frequency and hybridoma forming rate when an ac signal is applied to the chamber as shown in FIGS. 2a and 2b.

FIG. 6 shows the formation rate of hybridoma colonies obtained by applying to the chamber of FIG. 1 after centrifugation an ac signal having a voltage of 12 kV/cm, the application time being 600 microsec, the number of applied stimulation being 1, the frequency of the ac signal being a variable. The number of hybridoma colonies per $2.5 \times 10^5$ myeloma cells was the largest (9 to 10) near 10 kHz and slightly decreases at 5 kHz. The trend of decreasing was obvious from 20 to 50 kHz, and at 100 kHz, the forming rate was reduced to about the half of it obtained at 10 kHz. At 250 and 500 kHz, hybridoma colonies were hardly formed. It demonstrates that the effect of electroporation is lost when the frequency is higher than a certain value. Particularly, it is assumed that a high frequency wave such as 500 kHz passes through the cells without causing damage.

C. Application time condition

Figure 7:
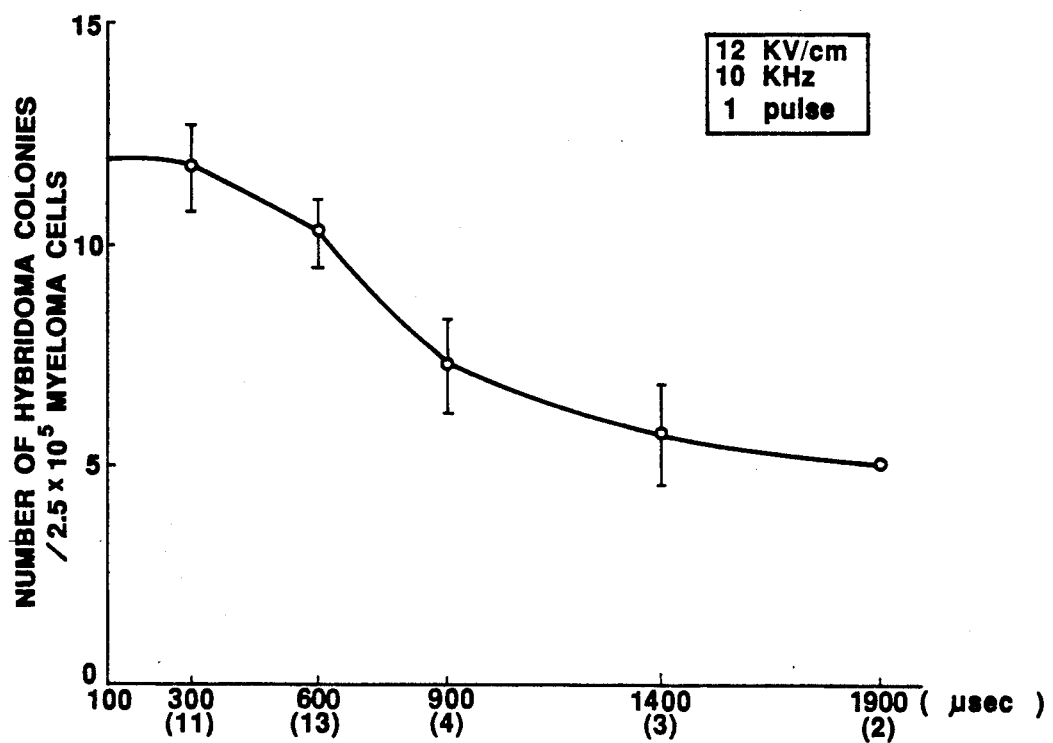
FIG. 7 is a graph showing a relationship between the stimulation applying time and hybridoma forming rate when an ac signal is applied to the chamber as shown in FIGS. 2a and 2b.

FIG. 7 shows the formation rate of hybridoma colonies obtained by applying to the chamber of FIG. 1 after centrifugation an ac signal having a voltage of 12 kV/cm and a frequency of 10 kHz, the number of applied stimulation being 1, the application time of the ac signal being a variable. The number of hybridoma colonies per $2.5 \times 10^5$ myeloma cells was 11 to 13 near 300 microsec and 9 to 11 at 600 microsec and decreased gradually as the application time became longer. It is assumed that an excessive amount of energy contained in one stimulation affected the survival of cells.

D. Stimulation number condition

Figure 8:
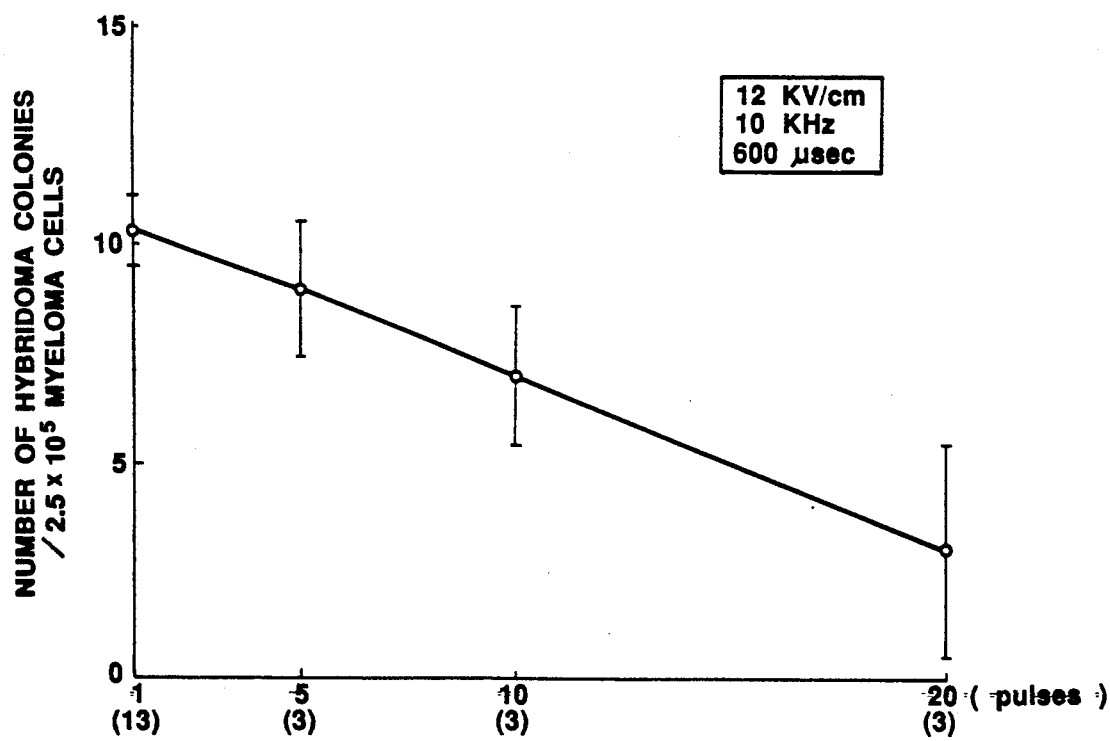
FIG. 8 is a graph showing a relationship between the number of applied stimulation and hybridoma forming rate when an ac signal is applied to the chamber as shown in FIGS. 2a and 2b.

FIG. 8 shows the formation rate of hybridoma colonies obtained by applying to the chamber of FIG. 1 after centrifugation an ac signal having a voltage of 12 kV/cm and a frequency of 10 kHz, the application time being 600 microsec, the stimulation interval of FIG. 4 being 1 second, the number of applied stimulation being a variable. Colonies were most effectively formed when the number of applied stimulation was 1 (9 to 11 hybridoma colonies/$25 \times 10^5$ myeloma cells). From 2 to 5 times, although a decreasing trend was observed, there was no significant difference. From 10 to 20 times, the number of colonies was reduced slowly to about the half of it obtained by one stimulation.

The present invention is not limited to the above examples, and various modifications may be made in the scope of the appended claims. For instance, in Example 2, the chamber after centrifugation may be supplied with a dc pulse, as in a conventional method, instead of an ac signal under certain conditions. Further, the dimension of the chamber may be modified in accordance with the size, type, concentration, etc., of the cells to be fused.

Moreover, in Example 5, although the centrifugation method with the chamber of Example 1 was used to test the effect of electroporation under various conditions of the ac signal, a conventional apparatus and method for dielectrophoresis may be used. In this case, at least two cells in the suspension can be aligned and fused by controlling the ac conditions only, so that the apparatus can be small.

What is claimed is:

1. A device for fusing biological cells in a solution by applying a voltage, comprising:
   a tube having an upper open end, a lower open end, and a side wall between the upper and lower open ends;
   a lower electrode having a flat surface attached tightly to the lower open end of the tube;
   a cover mounted tightly and detachably on the upper open end of the tube; and
   an upper electrode penetrating through the cover and extending to the vicinity of the flat surface of the lower electrode with a space remaining between the upper electrode and the side wall of the tube.

2. The device of claim 1, wherein the tube has the same diameter from the upper open end to the lower open end.

3. The device of claim 1, wherein the diameter of the tube is gradually enlarged upward from the lower open end.

4. The device of claim 1, wherein the upper electrode is in the form of a rod and has a semispheric end surface.

5. The device of claim 1, wherein the upper electrode is movable upwards and downwards through the cover and adjustably secured with a screw.

6. The device of claim 1, wherein the lower electrode is cylindrical and protrudes from the lower open end of the tube.

* * * * *